(12) United States Patent
Karp (10) Patent No.: US 7,833,142 B2
(45) Date of Patent: Nov. 16, 2010

(54) METHODS AND APPARATUS FOR TESTING ABDOMINAL STRENGTH AND EXERCISING ABDOMINAL MUSCLES

(76) Inventor: Shaun A. Karp, P.O. Box 47518, Coquitlam, BC (CA) V3K 6T3

(*) Notice: Subject to any disclaimer, the term of this patent is extended or adjusted under 35 U.S.C. 154(b) by 257 days.

(21) Appl. No.: 11/996,288

(22) PCT Filed: Jul. 19, 2006

(86) PCT No.: PCT/CA2006/001185

§ 371 (c)(1),
(2), (4) Date: May 9, 2008

(87) PCT Pub. No.: WO2007/009244

PCT Pub. Date: Jan. 25, 2007

(65) Prior Publication Data

US 2008/0214372 A1 Sep. 4, 2008

(51) Int. Cl.
*A63B 26/00* (2006.01)
(52) U.S. Cl. .......................... 482/140; 482/23; 446/220
(58) Field of Classification Search ................ 482/140, 482/91, 907, 142, 1–9, 111; 601/26, 148, 601/49, 56–60; 600/587, 594; 297/284.1, 297/284.7; 340/573.1, 573.7; 5/621, 630, 5/636–638, 640, 922, 940
See application file for complete search history.

(56) References Cited

U.S. PATENT DOCUMENTS

| 515,865 | A | * | 3/1894 | Scanlon ................ 229/123.2 |
| 3,325,799 | A | | 6/1967 | Farris |
| 4,326,506 | A | | 4/1982 | Kawabata |
| 4,759,543 | A | | 7/1988 | Feldman |
| 4,905,990 | A | | 3/1990 | DeSantis |
| 5,304,109 | A | | 4/1994 | Shockley |
| 5,338,276 | A | * | 8/1994 | Jull et al. .................... 482/113 |
| 5,515,865 | A | | 5/1996 | Scanlon |

(Continued)

FOREIGN PATENT DOCUMENTS

WO  0126506 A2  4/2001

(Continued)

OTHER PUBLICATIONS

International Search Report for PCT/CA2006/001185, International Searching Authority, Nov. 22, 2006, pp. 1-4.

*Primary Examiner*—Lori Baker
(74) *Attorney, Agent, or Firm*—Oyen Wiggs Green & Mutala LLP (57) ABSTRACT

An abdominal mat has a raised section which may be positioned to support the lumbar region of the user's back. At least one sensor is associated with the raised section for producing a signal in response to force applied to the raised section by the user. A feedback device is coupled to the sensor for providing feedback to the user based on the force applied to the raised section. A user may use the device to test the strength of his or her abdominal muscles, and/or to monitor the force applied to the raised section of the mat when the user is exercising his or her abdominal muscles. The raised section may comprise an inflatable bladder connected to be automatically inflated and deflated by an electronic pump to accommodate different body types, therefore establishing a consistent starting point.

31 Claims, 8 Drawing Sheets

U.S. PATENT DOCUMENTS

| | | | |
|---|---|---|---|
| 5,674,238 A * | 10/1997 | Sample et al. | 606/192 |
| 5,755,647 A * | 5/1998 | Watnik | 482/142 |
| 5,785,669 A * | 7/1998 | Proctor et al. | 601/148 |
| 5,845,644 A | 12/1998 | Hughes et al. | |
| 6,019,738 A * | 2/2000 | Brandon | 600/587 |
| 6,117,095 A | 9/2000 | Daggett et al. | |
| 6,384,729 B1 | 5/2002 | Plotkin | |
| 6,479,727 B1 | 11/2002 | Roe | |
| 6,648,838 B1 * | 11/2003 | Brandon et al. | 600/587 |
| 6,876,883 B2 | 4/2005 | Hurtado | |
| 2001/0020143 A1 | 9/2001 | Stark et al. | |
| 2002/0098958 A1 | 7/2002 | Watnik | |
| 2004/0056520 A1 | 3/2004 | Cho | |
| 2004/0097837 A1 | 5/2004 | Brandon et al. | |
| 2004/0152957 A1 | 8/2004 | Stivoric et al. | |
| 2004/0195876 A1 | 10/2004 | Huiban | |
| 2004/0201487 A1 | 10/2004 | Benson et al. | |
| 2005/0043660 A1 | 2/2005 | Stark et al. | |
| 2005/0137462 A1 | 6/2005 | Cho | |
| 2006/0132382 A1 | 6/2006 | Jannard | |
| 2006/0150752 A1 | 7/2006 | Lorenz et al. | |
| 2006/0208169 A1 | 9/2006 | Breed et al. | |
| 2006/0265941 A1 | 11/2006 | Newton | |

FOREIGN PATENT DOCUMENTS

| | | |
|---|---|---|
| WO | 2004002313 A1 | 1/2004 |

* cited by examiner

METHODS AND APPARATUS FOR TESTING ABDOMINAL STRENGTH AND EXERCISING ABDOMINAL MUSCLES

TECHNICAL FIELD

The invention relates to abdominal fitness, and to exercise mats.

BACKGROUND

Proper abdominal strength is required to help maintain normal trunk posture and function as well as to prevent injury, particularly to the lower back. A variety of exercises can be utilized to strengthen the abdominal muscles. Such exercises include, but are not limited to: conventional sit ups, crunches (partial sit ups), leg raises lying supine (with knees bent or straight), torso twists, hanging leg raises, pelvic tilts, kneeling crunches using cable resistance, exercises using abdominal sit up machines, etc.

In the process of abdominal conditioning, it is desirable for the individual to do exercises appropriate for their level of abdominal strength and coordination to prevent injury and to facilitate optimal strengthening. There exist a number of prior art devices which a user may use to assist with exercising his or her abdominal muscles.

For example, U.S. Pat. No. 5,755,647 to Watnik discloses an exercise appliance which includes a structure presenting a resiliently yieldable contact surface having a contour suitably sized and shaped to be at least partially fittable in the space formed between a support surface and a static lordotic curve of a lumbar back of an individual. The appliance may also be provided with means for providing feedback in response to compression of the appliance.

Other examples of prior art apparatus relating to abdominal fitness include U.S. Pat. Nos. 6,648,838, 6,117,095, 6,019,738, 5,785,669, 5,515,865, 5,304,109, 4,905,990, 4,759,543, and 3,325,799, U.S. Patent Application Publications No. 2005/0043660 and No. 2001/0020143, and PCT Publications No. WO 2001/26506 and No. WO 2004/002313.

Although there exist devices designed to strengthen the abdominal muscles, and many exercises designed to do the same, the inventor has determined that there is a need for accurate abdominal muscle strength testing which is vital for appropriate exercise recommendations and is also useful for monitoring rehabilitation, research and the like.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention provides an abdominal strength testing and exercising device. The device comprises a support having a raised section for supporting a lumbar portion of a user's back, a sensor associated with the raised section of the support for producing a signal in response to a force applied to the raised section, and a feedback device adapted to received the signal from the sensor for providing the user with feedback when the force applied to the raised section exceeds a threshold.

Another aspect of the invention provides a method of testing a user's abdominal muscle strength. The method comprises providing a support having a raised section for supporting a lumbar portion of a user's back, receiving a user-selected threshold force, determining a force dependent value indicative of a force applied to the raised section, and providing feedback to the user if the force dependent value indicates that the force applied to the raised section is at least as strong as the user-selected threshold.

Further aspects of the invention and features of embodiments of the invention are described herein and/or shown in the accompanying drawings.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

In drawings which illustrate non-limiting embodiments of the invention.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

The invention provides devices for exercising and testing the strength of users' abdominal muscles. An example device comprises an abdominal mat. The mat has a raised section which may be positioned to support the lumbar region of the user's back. At least one sensor is provided for determining a force applied by the user to the raised section. A feedback device is coupled to the sensor. The feedback device provides feedback to the user or another person working with the user based on the force applied to the raised section. In some embodiments the feedback device comprises a display which indicates a magnitude of the applied force on a non-linear scale. A user may use the device to test the strength of his or her abdominal muscles, and/or to monitor the force applied to the raised section of the mat when the user is exercising his or her abdominal muscles.

Figure 1:
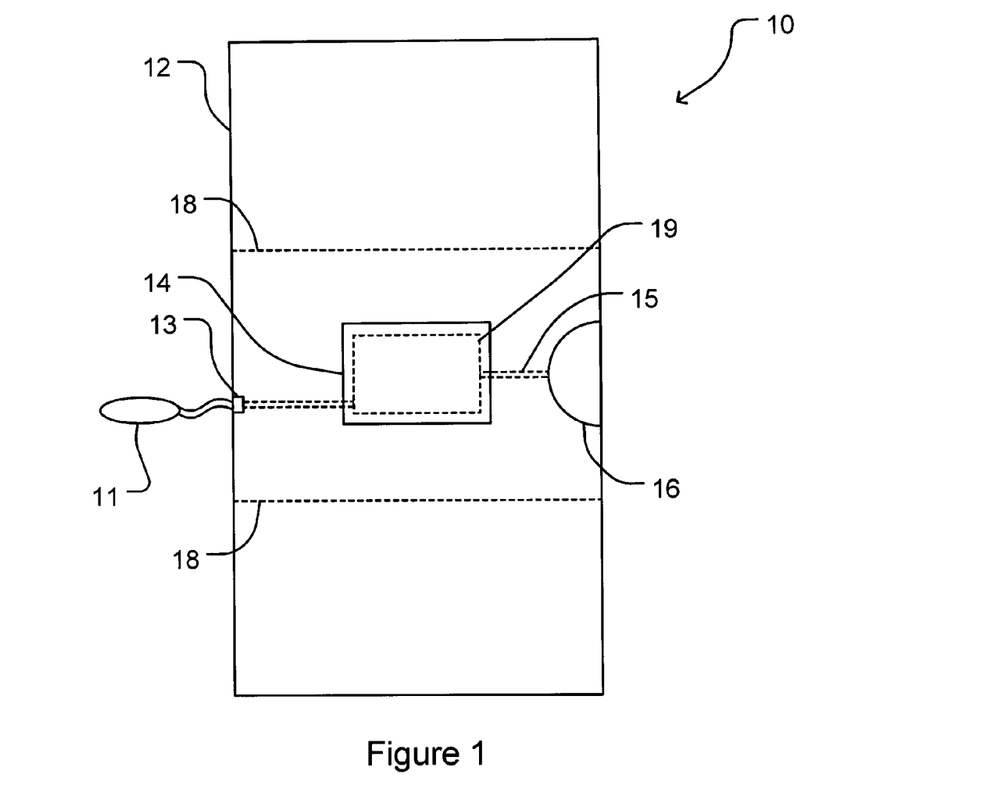
FIG. 1 is a top view of an exercising and strength testing device according to one embodiment of the invention.
Figure 2:
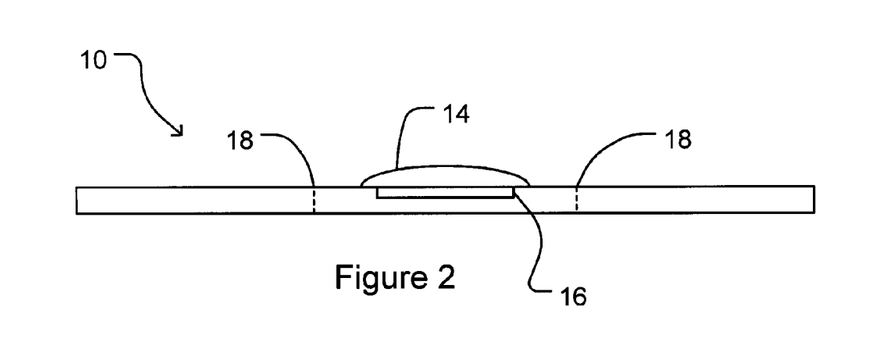
FIG. 2 is a side view of the device of FIG. 1.

FIGS. 1 and 2 show a device 10 according to one embodiment of the invention. Device 10 comprises a mat 12 having a raised section 14. Raised section 14 is positioned to support the lumbar region of a user's back when the user lies on mat 12. A feedback device 16 is embedded in mat 12 and coupled to raised section 14 by means of a connector 15. Mat 12 may be foldable as indicated by fold lines 18. Fold lines 18 may or may not be symmetrically positioned with respect to mat 12 or raised section 14.

In the embodiment of FIGS. 1 and 2, raised section 14 comprises an inflatable bladder 19 filled with a fluid, such as for example, air. Device 10 may also comprise means for varying the pressure in inflatable bladder 19, such as for example, a hand pump 11 coupled to inflatable bladder 19 through a valve assembly 13. Valve assembly 13 may be configured to seal to prevent fluid from escaping from inflatable bladder 19 when hand pump 11 is removed from mat 12. Valve assembly 13 also allows the user to bleed air or other fluid out of inflatable bladder 19 to reduce the pressure of the fluid in inflatable bladder 19. The user may use hand pump 11 and valve assembly 13 to select a desired initial pressure of the fluid in raised section 14. The desired pressure may be, for example, about 50 to 60 mmHg (relative to atmospheric pressure). The amount of fluid will depend on the user's size and body type as well as on the dimensions of raised section 14. It has been found that a pressure of about 60 mmHg is satisfactory for use by users having a wide range of body sizes and types.

A basic pressure of 60 mmHg allows a person to maintain a neutral spine posture while also feeling sufficient pressure from bladder 19 against the lower back to be able to use device 10 effectively. If the pressure in bladder 19 is too low then the person's spine will tend to flatten out. This, in turn, may provide results that do not indicate abdominal strength available for activities conducted with the spine in a neutral posture (as is the case for most day-to-day activities).

Device 10 also comprises one or more sensors 22 (see FIG. 6) associated with raised section 14. The sensor(s) are configured to produce a signal in response to force applied to raised section 14, and may be positioned in, on, or under raised section 14, in mat 12 adjacent raised section 14, in connector 15, or in feedback device 16. In one configuration, a sensor 22 senses a pressure within bladder 19. In some embodiments, connector 15 comprises a hose in fluid communication with the inside of inflatable bladder 19 of raised section 14, and a sensor is provided in feedback device 16 for measuring the pressure of the fluid in the hose. Alternatively, a pressure sensor could be positioned in fluid communication with bladder 19 in a suitable location such as in connector 15, directly within inflatable bladder 19 of raised section 14, or adjacent to inflatable bladder 19. In the further alternative, a force sensor may be provided on raised section 14 to measure directly a force applied to raised section 14 by a user's lower back.

Figure 3:
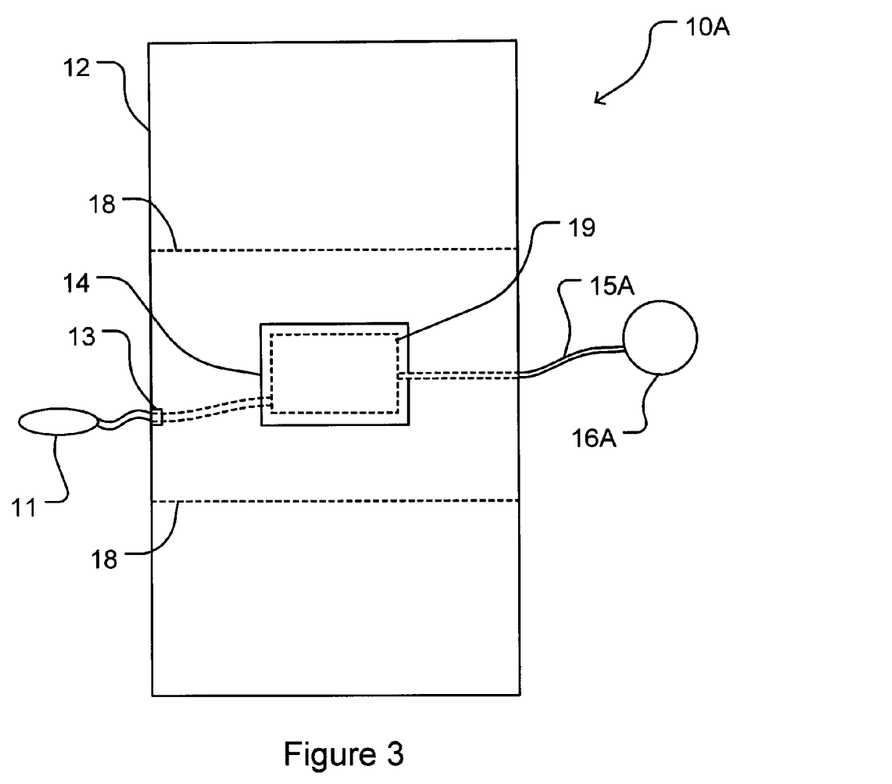
FIG. 3 is a top view of an exercising and strength testing device according to another embodiment of the invention.
Figure 4:
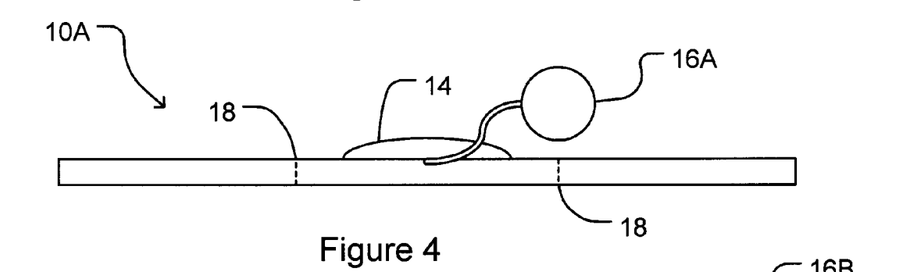
FIG. 4 is a side view of the device of FIG. 3.

FIGS. 3 and 4 show a device 10A according to another embodiment of the invention. Device 10A is the same as device 10 of FIGS. 1 and 2, except that in device 10A feedback device 16A is external to mat 12, rather than embedded therein. Feedback device 16A may be supported on a tripod, folding stand, or the like to allow the user to see feedback device 16A when lying on mat 12.

Figure 5:
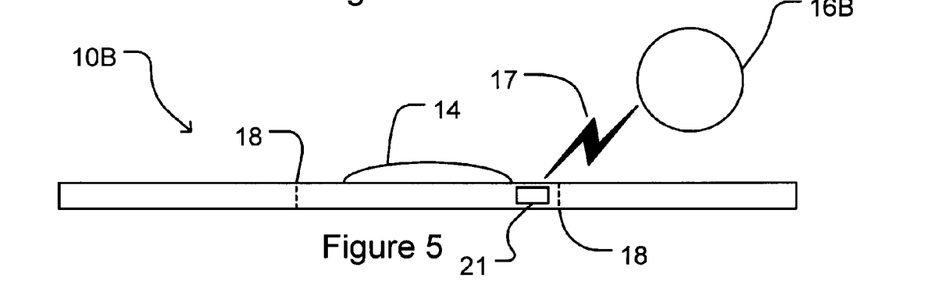
FIG. 5 is a side view of an exercising and strength testing device according to another embodiment of the invention.

FIG. 5 shows a device 10B according to another embodiment of the invention. Device 10B is the same as device 10A of FIGS. 3 and 4, except that in device 10B connector 15A is replaced with a wireless communication link 17, and one or more pressure sensors and a wireless transmitter 21 coupled to a power source (not shown) are embedded in mat 12 (or raised section 14). Transmitter 21 may comprise an antenna (not shown) embedded in mat 12, depending on the distance between transmitter 21 and feedback device 16B. In the FIG. 5 embodiment, signals from the one or more sensors are provided to transmitter 21 and sent to feedback device 16B by means of communication link 17.

Figure 6:
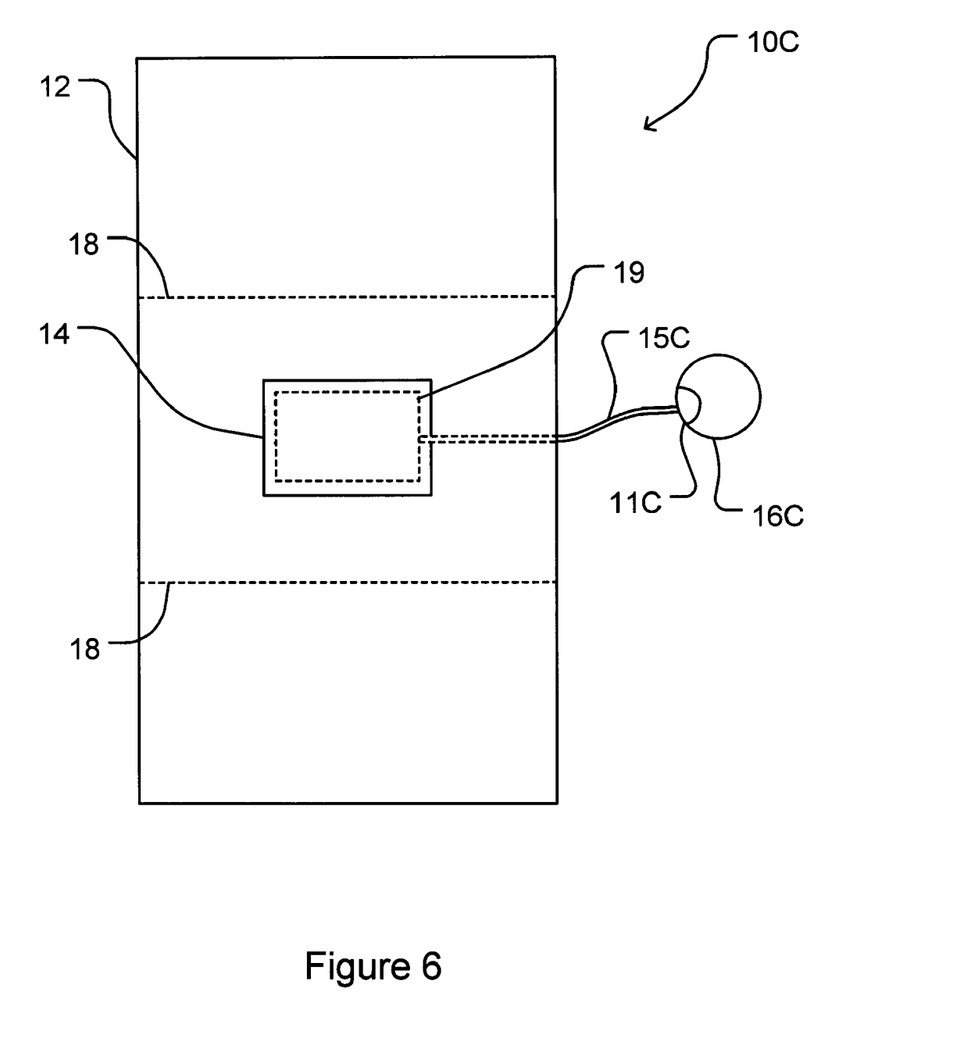
FIG. 6 is a top view of an exercising and strength testing device according to another embodiment of the invention.

FIG. 6 shows a device 10C according to another embodiment of the invention. Device 10C is the same as device 10A of FIGS. 3 and 4, except that in device 10C hand pump 11 and valve assembly 13 are omitted, and an electronic pump 11C is incorporated into feedback device 16C. Pump 11C is in fluid communication with bladder 19 by means of connector 15C. Pump 11C is controlled to automatically inflate (or inflate and deflate) bladder 19 under the control of feedback device 16C. Pump 11C may be controlled in response to a signal from a pressure sensor. The pressure sensor may be integrated with pump 11C or may be otherwise situated to measure pressure within bladder 19.

Figure 6A:
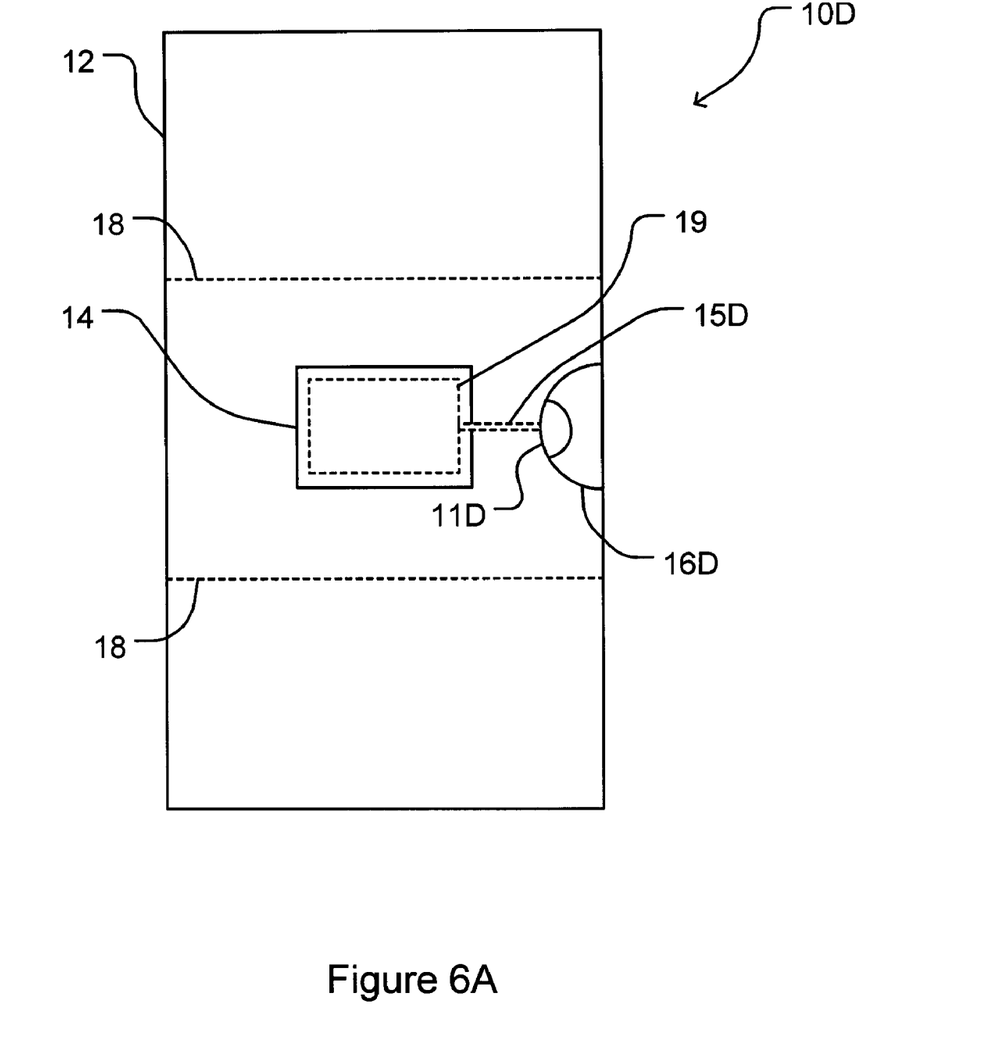
FIG. 6A is a top view of an exercising and strength testing device according to another embodiment of the invention.

In some embodiments, a user prepares device 10C for use by lying on mat 12 in a neutral posture. Either in response to detecting the presence of the user by way of a suitable sensor or in response to the user pressing a button, switch or the like, feedback device 16C causes pump 11C to automatically inflate or deflate bladder 19 to fit the contour of a variety of users large or small so that bladder 19 has a consistent starting pressure in the range of about 50 to 60 mmHg (or some other desired pressure)—preferably about 60 mmHg. When the desired pressure has been reached, feedback device 16C generates a user-detectable signal (such as making a sound, providing tactile feedback, turning on an indicator lamp, or the like) that indicates that device 10C is ready for use. FIG. 6A shows a device 10D according to another embodiment of the invention. Device 10D is the same as device 10C except feedback device 16D and pump 11D are incorporated into mat 12.

Figure 7:
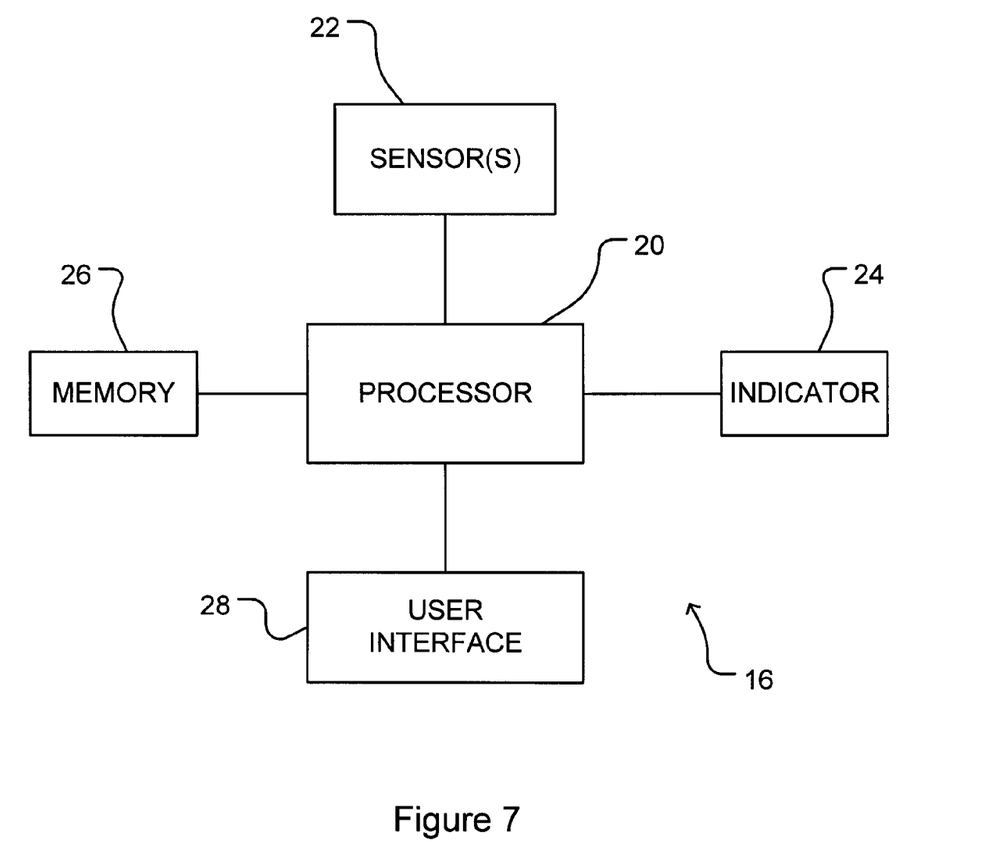
FIG. 7 schematically illustrates the components of a feedback device according to one embodiment of the invention.

FIG. 7 shows an example configuration of feedback device 16 of FIGS. 1 and 2. Feedback device 16A, 16B, or 16C could have a configuration similar to feedback device 16. Feedback device 16 comprises a processor 20 adapted to receive signals from one or more sensors 22 associated with raised section 14. As discussed above, sensors 22 may be positioned in, on or under raised section 14, in mat 12 adjacent raised section 14, in connector 15, or in feedback device 16. Sensors 22 may comprise either analog or digital sensors. Processor 20 determines from the signals from sensors 22 a force-dependent value which is indicative of a force being applied by the user on raised section 14.

Feedback device 16 also comprises an indicator 24 which provides feedback to the user under control of processor 20. Indicator 24 may comprise, for example, an audible indicator such as a buzzer or a speaker, or a visual indicator such as a display screen or a series of lights. In some embodiments indicator 24 comprises a bar graph, a pointer which moves along a scale (the scale may be straight or curved). In some embodiments indicator 24 comprises both audible and visible indicators. In some embodiments, indicator 24 displays a number, or the like words or other indicia that indicate an amount of force being measured by sensors 22.

In preferred embodiments, indicator 24 comprises a nonlinear scale. One such scale is shown in Table I. Table I assumes that a sensor 22 measures a fluid pressure in bladder 19 and that the feedback is indicated on a scale having a minimum value of zero and a maximum value of 10. Separate scales are provided for men and women.

TABLE I

| MEN(mmHg) | WOMEN (mmHg) | Scale value |
|---|---|---|
| 60 | 60 | 0 |
| 70 | 65 | 1 |
| 80 | 75 | 2 |
| 90 | 85 | 3 |
| 100 | 95 | 4 |
| 120 | 110 | 5 |
| 140 | 125 | 6 |
| 160 | 140 | 7 |
| 185 | 155 | 8 |
| 215 | 180 | 9 |
| 245 | 210 | 10 |

On the scale of Table I, a strength level of "1" indicates very weak abdominal muscles. A strength level of "10" indicates exceedingly strong abdominal muscles. An elite athlete could possibly have a strength level of "10". In the scale of Table I, zero on the scale corresponds to a positive pressure (60 mmHg in this example) and the pressure increment required to reach the next value on the scale increase as the scale values increase.

In some embodiments, multiple graduated scales may be provided. For example, scales may be provided for "beginner", "intermediate", and "advanced" users. A separate scale may be provided for any defined population of users. for example, separate scales may be provided for elite hockey players, male fire fighters or the like.

The same pressure may correspond to zero on each of the scales. The pressures corresponding to a maximum scale value (e.g. "10") may increase from scale-to-scale. A knob, button, switch or other control may be provided to allow a user to select an appropriate scale from the plurality of scales.

The scales may each comprise a median normalized strength scale based on a population study of users of a given level (i.e. beginner, intermediate, advanced). For each level, separate scales may be provided for men and women. The strength level on each non-linear scale may correspond to a percentile rank within that user level (e.g. a strength level of "5" may indicate that the pressure exerted by the user indicates that the strength of the user's abdominal muscles is in the 50th percentile for a population made up of all users belonging to the user level to which the scale corresponds).

Processor 20 may be coupled to a memory 26 storing computer-readable instructions, such that processor 20 may implement methods according to the invention by executing the computer-readable instructions. Processor 20 may also maintain a log of signals from sensors 22 in memory 26. Processor 20 may also be configured to communicate with a computer running software to allow the user to interact with processor 20 and any log stored in memory 26.

Feedback device 16 may also comprise a user interface 28 which may be used by the user to interact with processor 20. User interface 28 may comprise, for example, a dial or a switch with multiple settings. Alternatively or additionally, user interface 28 may comprise a keypad and a display (which may be the same display as used by a visual indicator 24). The display may comprise a plurality of LEDs for indicating a user's strength level on a selected scale, for setting a threshold or a target range, and for indicating the operational mode of device 10. the user may use user interface 28 to turn device 10 on and off, to select between a threshold operation mode and a target operation mode, and to set threshold or target forces, as described below.

In operation, a user lies down on mat 12 and positions raised portion 14 under the curve of his or her spine (i.e., under the lumbar region of the user's back). In embodiments comprising an electronically-controlled pump, such as the embodiment of FIG. 6, the pump may operate automatically to inflate or deflate bladder 19 to achieve the desired pressure while the user is lying in a neutral position. An audible and/or visible indication may indicate to the user that the desired pressure has been achieved. The user then selects a scale for measuring strength levels and an operation mode and begins to do exercises.

In the threshold mode, the user may either input a force threshold or select one of a plurality of predetermined force thresholds. For example, in embodiments where feedback device 16 (or 16A or 16B or 16C) comprises a dial, the user may move the dial to select one of ten predetermined thresholds (or some other number of predetermined thresholds).

In the threshold mode, device 10 provides the user with feedback when a user-selected threshold of force is reached or exceeded by the user pressing his or her lower back against raised section 14. For example, in embodiments where feedback device 16 comprises an audible indicator, the feedback may comprise a sound such as a beep or a buzz which is generated when the applied force exceeds the threshold, or may comprise a recorded voice which states a value indicative of the applied force, or states some other message such as, for example, "threshold achieved." In embodiments where feedback device 16 comprises a visual indicator, the feedback may comprise, for example, displaying a number or a bar graph indicative of the applied force, or lighting a number of LEDs corresponding to a user's strength level measured on a selected scale. The threshold mode is useful for testing abdominal strength, since the user can determine how high they can set the threshold and still receive feedback from device 10 that indicates that the threshold has been achieved.

In the target mode, device 10 provides the user with feedback when the force applied by the user pressing their lower back against raised section 14 falls outside of a user-selected target range. In the target mode, the user may either input a target range or select from one of a plurality of predetermined target ranges. For example, in embodiments where feedback device 16 (or 16A or 16B or 16C) comprises a dial, the user may move the dial to select one of five predetermined ranges (or some other number of predetermined ranges). In the target mode, device 10 provides the user with feedback when the force exerted by the user pressing his or her lower back against raised section 14 is outside of the user-selected range. For example, in embodiments where feedback device 16 comprises an audible indicator, the feedback may comprise a sound such as a beep or a buzz which is generated when the applied force falls outside of the range, and may also comprise a warning sound generated when the applied force approaches a boundary of the range. In embodiments where feedback device 16 comprises a visual indicator, the feedback may comprise, for example, displaying a number or a bar graph indicative of the applied force or lighting a number of LEDs corresponding to a user's strength level measure on a selected scale. The target mode is useful for doing exercises where it is desirable to maintain a relatively constant pressure on raised section 14, such as for example leg lifts.

Figure 8:
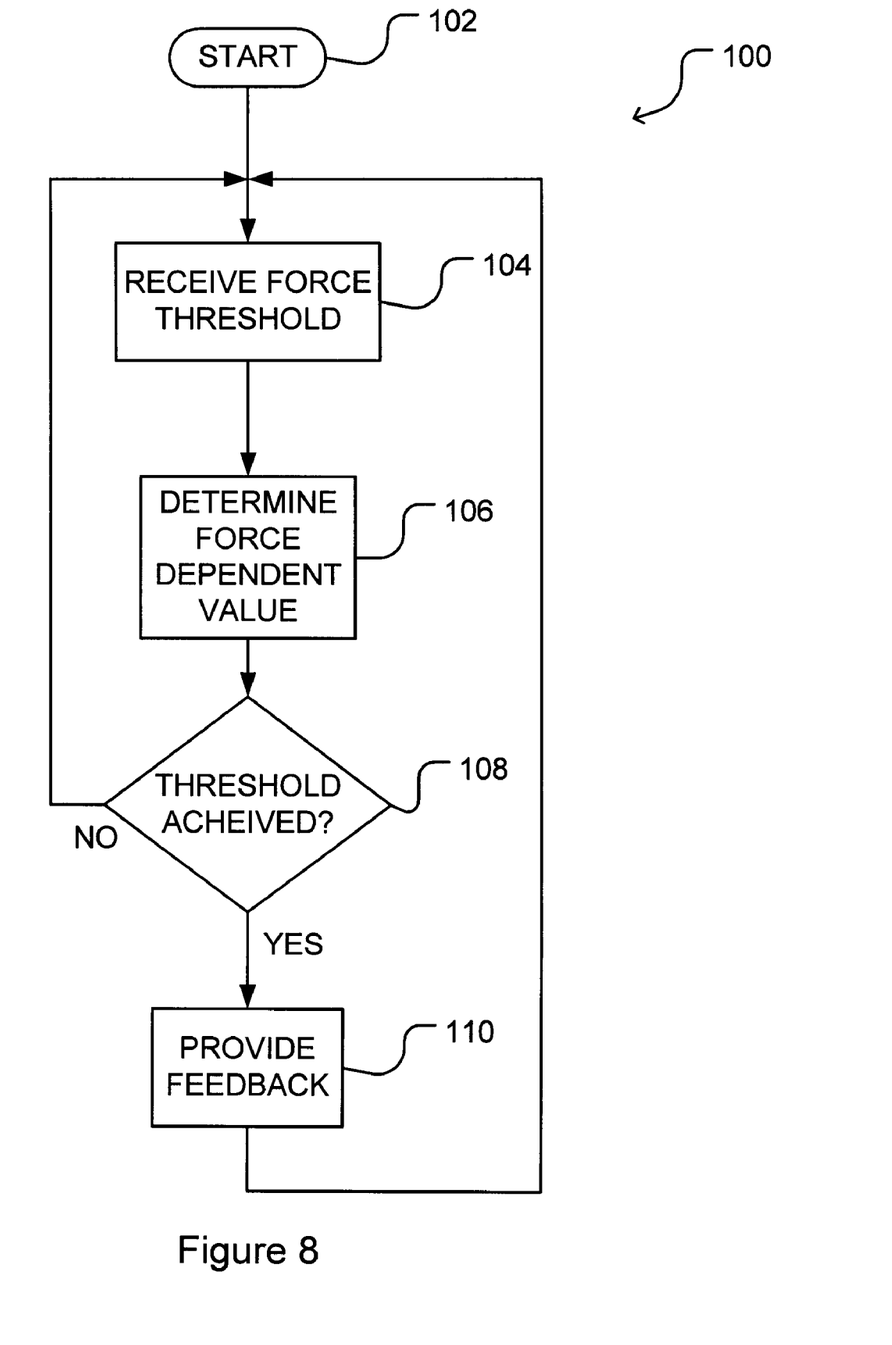
FIG. 8 is a flowchart illustrating a method according to one embodiment of the invention.

FIG. 8 illustrates a method 100 of providing feedback to the user of an abdominal exercising and strength testing device in a threshold operation mode. Method 100 is described with reference to device 10 of FIGS. 1, 2 and 7, but it is to be understood that method 100 could be carried out with a different embodiment of the invention.

Method 100 starts at block 102, for example by the user turning on device 10 and selecting the threshold operation mode. At block 104 processor 20 receives information specifying a force threshold from user input 28. At block 106 a force dependent value indicative of the applied force on raised section 14 is determined by processor 20 based on signals from sensors 22. At block 108 processor determines if the force dependent value determined at block 106 indicates that the force applied to raised section 14 is at least as strong as the threshold force received at block 104. If not (block 108 NO output), method 100 repeats the steps of blocks 104 to 108. If the force dependent value determined at block 106 indicates that the force applied to raised section 14 is at least as strong as the force threshold received at block 104 (block 108 YES output), method 100 proceeds to block 110 where processor 20 causes indicator 24 to provide feedback to the user indicating that the force threshold has been reached. Method 100 then returns to block 104. In some situations, the user may wish to do multiple repetitions of an exercise using the same force threshold. In such situations, the user can select the force threshold initially using user input 28, then leave the force threshold set while exercising.

Figure 9:
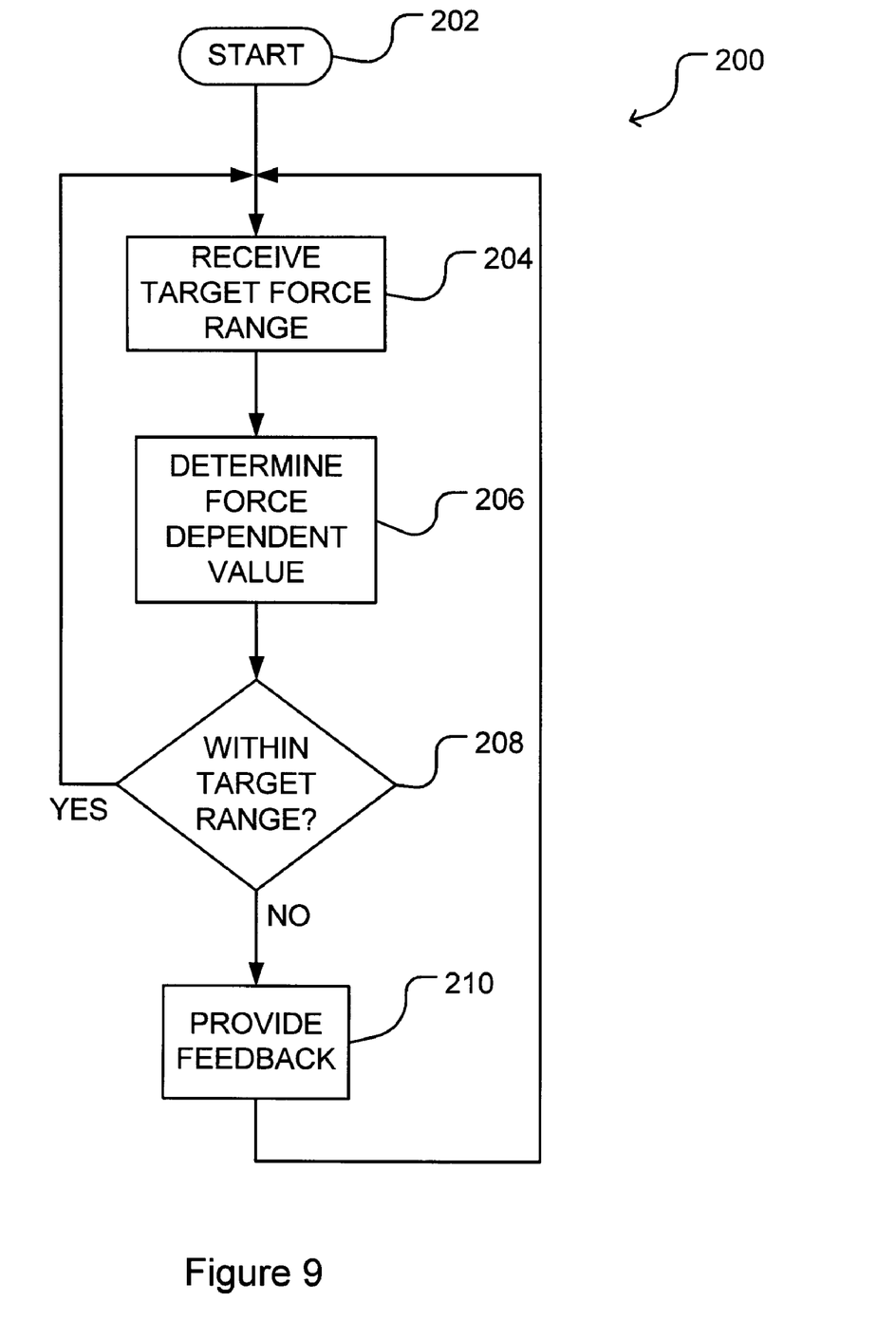
FIG. 9 is a flowchart illustrating a method according to another embodiment of the invention; and, FIG. 10 shows a bench according to another embodiment of the invention.

FIG. 9 illustrates a method 200 of providing feedback to the user of an abdominal exercising and strength testing device in a target operation mode. Method 200 is described with reference to device 10 of FIGS. 1, 2 and 7, but it is to be understood that method 200 could be carried out with a different embodiment of the invention.

Method 200 starts at block 202, for example by the user turning on device 10 and selecting the target operation mode. At block 204 processor 20 receives information specifying a target force range from user input 28. At block 206 a force dependent value indicative of the applied force on raised section 14 is determined by processor 20 based on signals from sensors 22. At block 208 processor determines if the force dependent value determined at block 206 indicates that the force applied to raised section 14 is within the target force range received at block 204. If it is (block 208 YES output), method 200 repeats the steps of blocks 204 to 208. If the force dependent value determined at block 206 indicates that the force applied to raised section 14 is outside of the target force range received at block 204 (block 208 NO output), method 200 proceeds to block 210 where processor 20 causes indicator 24 to provide feedback to the user, indicating that the user is applying force to raised section 14 outside of the target force range. Method 200 then returns to block 204.

In an example embodiment, a user first sets a strength level. This may be achieved by selecting a threshold as described above and pressing down on raised section 14. Device 10 beeps if the threshold is achieved. The user can increase the threshold until he or she determines the largest achievable threshold. Next, the user places device 10 in a strength mode. In this mode the user may perform repetitions of an exercise. In each repetition the user works to cause device 10 to beep, thus indicating that the user has achieved a set pressure. In a third mode the user can perform an exercise which requires the user to maintain a steady pressure on raised section 14. In this mode device 10 beeps if the user is pushing too hard or not hard enough.

Figure 10:
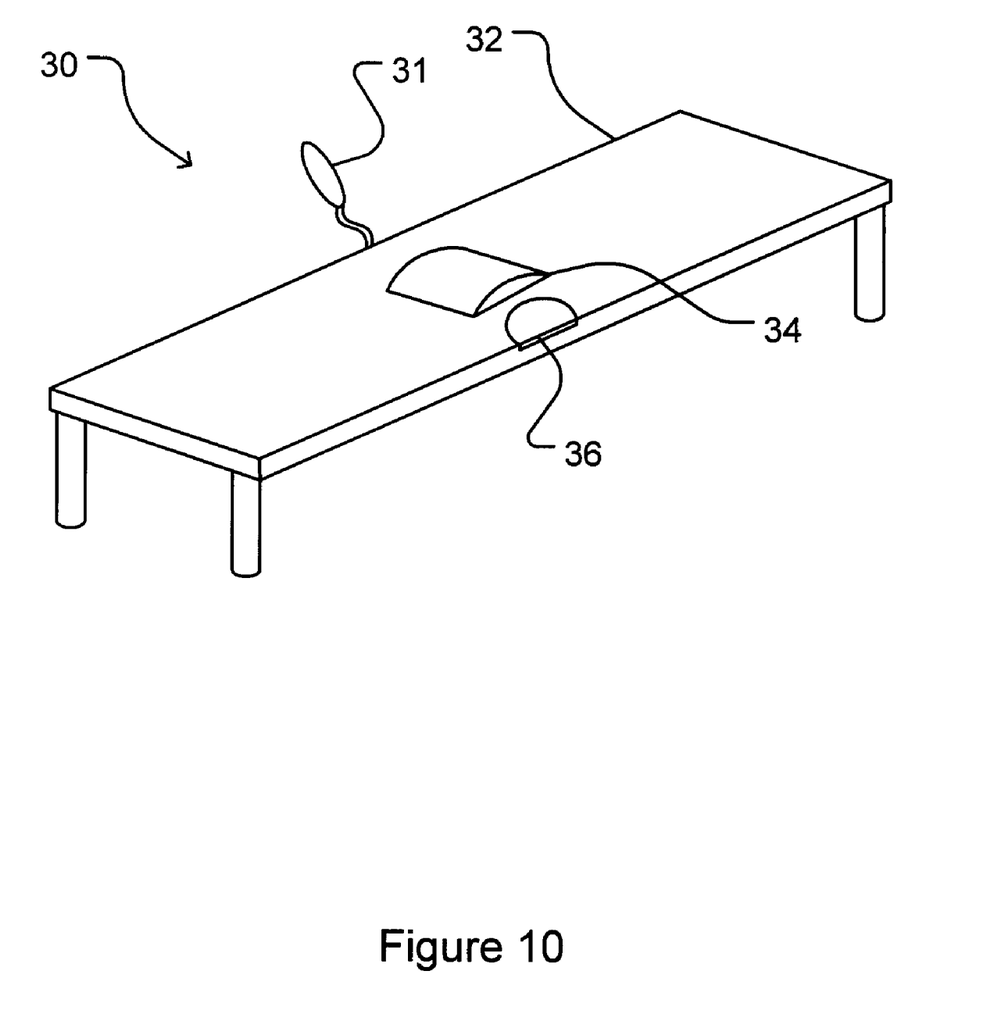

A structure other than a mat may be used as a support for the user's back. For example, FIG. 10 shows a device 30 according to another embodiment of the invention. Device 30 comprises a bench 32 having a raised section 34. Raised section 34 may be inflated using hand pump 31, and is coupled to feedback device 36. Device 30 functions just like device 10 of FIGS. 1 and 2, except that bench 32 is not foldable.

A device 10 as described herein responds primarily to forces exerted by a user's lower abdominal muscles. This is advantageous since weakness in the lower abdominal muscles can be a cause of certain kinds of back pain. The strength of the upper abdominal muscles is not highly relevant to such kinds of back pain.

A device as described herein may be used to assess the strength of a person's lower abdominal muscles and to provide objective measurements of changes in strength of the person's lower abdominal muscles over time.

While a number of exemplary aspects and embodiments have been discussed above, those of skill in the art will recognize certain modifications, permutations, additions and sub-combinations thereof. For example:

- although the drawings show a rectangular mat, the mat may have a different shape;
- the fluid in bladder 19 may comprise a liquid such as water, or oil, or the like or a mixture of air (or another gas) and a liquid;
- the various embodiments described herein each have various features that can be combined in combinations or sub combinations other than those that are expressly described herein.

It is therefore intended that the following appended claims and claims hereafter introduced are interpreted to include all such modifications, permutations, additions and sub-combinations as are within their true spirit and scope.

What is claimed is:

1. An abdominal exercising and strength testing device comprising:
    a support having a raised section for supporting a lumbar portion of a user's back, the raised section comprising an inflatable bladder;
    a sensor associated with the raised section of the support for producing a signal representative of a magnitude of a force applied to the raised section;
    a pump in fluid communication with the bladder, the pump connected to receive the signal from the sensor and automatically pressurize the bladder to a desired pressure based on the signal;
    a feedback device adapted to receive the signal from the sensor for providing the user with feedback based on the magnitude of the force applied to the raised section, the feedback comprising a strength level measured on a non-linear scale;
    a user interface for receiving: a user-selected operation mode from among a plurality of operation modes comprising a threshold mode and a target mode; a user-selected force threshold; and a user selected target force range;
    a processor coupled to the sensor and to the user interface; and
    a memory coupled to the processor, the memory containing computer-readable instructions which, when executed by the processor, cause the processor to:
        if the user-selected operation mode is the threshold mode, operate the feedback device to provide feedback when the force applied to the raised section exceeds the user-selected force threshold; and,
        if the user-selected operation mode is the target mode, operate the feedback device to provide feedback when the force applied to the raised section is outside of the user-selected target force range.

2. A device according to claim 1 wherein the feedback device comprises a user interface comprising a control operable for selecting one of a plurality of scales for measuring the strength level.

3. A device according to claim 2 wherein each of the plurality of scales comprises a normalized scale based on a population of users having similar fitness levels.

4. A device according to claim 3 wherein the strength levels on each of the plurality of scales correspond to percentile ranks within the population for that scale.

5. A device according to claim 1 wherein the feedback device comprises an audible indicator for providing the user with audible feedback and wherein the feedback device causes the audible indicator to emit a distinctive sound when the force applied to the raised section exceeds a first threshold.

6. A device according to claim 5 wherein the feedback device causes the audible indicator to emit a distinctive sound when the force applied to the raised section is less than a second threshold which is lower than the first threshold.

7. A device according to claim 6 wherein the feedback device comprises a visual indicator for providing the user with visible feedback.

8. A device according to claim 7 wherein the visual indicator comprises a representation of the non-linear scale and an indicia indicating the strength level.

9. A device according to claim 7 wherein the visual indicator is locatable in a position viewable by the user when lying on the support.

10. A device according to claim 2 wherein the memory is configured for storing one or more previously measured strength levels for a user.

11. A device according to claim 1 wherein the sensor comprises a pressure sensor in fluid communication with the inflatable bladder.

12. A device according to claim 1 wherein the desired pressure is about 60 mmHg.

13. A device according to claim 1 wherein a strength level of zero on the non-linear scale corresponds to a non-zero pressure.

14. A device according to claim 13 wherein, in the non-linear scale, the following pressures correspond to the following strength levels:
a pressure of 60 mmHg corresponds to a strength level of 0;
a pressure of 65 mmHg corresponds to a strength level of 1;
a pressure of 75 mmHg corresponds to a strength level of 2;
a pressure of 85 mmHg corresponds to a strength level 3;
a pressure of 95 mmHg corresponds to a strength level of 4;
a pressure of 110 mmHg corresponds to a strength level of 5;
a pressure of 125 mmHg corresponds to a strength level of 6;
a pressure of 140 mmHg corresponds to a strength level of 7;
a pressure of 155 mmHg corresponds to a strength level of 8;
a pressure of 180 mmHg corresponds to a strength level of 9; and
a pressure of 210 mmHg corresponds to a strength level of 10.

15. A device according to claim 13 wherein, in the non-linear scale, the following pressures correspond to the following strength levels:
a pressure of 60 mmHg corresponds to a strength level of 0;
a pressure of 70 mmHg corresponds to a strength level of 1;
a pressure of 80 mmHg corresponds to a strength level of 2;
a pressure of 90 mmHg corresponds to a strength level of 3;
a pressure of 100 mmHg corresponds to a strength level of 4;
a pressure of 120 mmHg corresponds to a strength level of 5;
a pressure of 140 mmHg corresponds to a strength level of 6;
a pressure of 160 mmHg corresponds to a strength level of 7;
a pressure of 185 mmHg corresponds to a strength level of 8;
a pressure of 215 mmHg corresponds to a strength level of 9; and
a pressure of 245 mmHg corresponds to a strength level of 10.

16. A device according to claim 1 further comprising a hose in fluid communication with the inflatable bladder, wherein the sensor comprises a pressure sensor coupled to the hose.

17. A device according to claim 1 wherein the sensor comprises a pressure sensor embedded in the raised section.

18. A device according to claim 1 wherein the sensor comprises a pressure sensor coupled to a transmitter and a power source embedded in the raised section, and wherein the transmitter provides the signal to the feedback device through a wireless communication link.

19. A device according to claim 1 wherein the support comprises a mat.

20. A device according to claim 19 wherein the mat comprises a plurality of fold lines along which the mat can be folded.

21. A method of testing a user's abdominal muscle strength and exercising the user's abdominal muscles, the method comprising:
providing a support having a raised section for supporting a lumbar portion of a user's back;
receiving a user-selected operation mode, the operation mode comprising one of a threshold mode and a target mode;
if the user-selected operation mode is the threshold mode:
  receiving a user-selected force threshold;
  determining a force dependent value indicative of a force applied to the raised section; and
  providing feedback to the user if the force dependent value indicates that the force applied to the raised section is at least as strong as the user-selected threshold; and
if the user-selected operation mode is the target mode:
  receiving a user-selected target force range;
  determining the force dependent value indicative of the force applied to the raised section; and
  providing feedback to the user if the force dependent value indicates that the force applied to the raised section is outside the user-selected target force range.

22. A method according to claim 21 wherein providing feedback comprises providing audible feedback.

23. A method according to claim 21 wherein providing feedback comprises providing visual feedback.

24. A device according to claim 1 wherein the pump is configured to automatically inflate or deflate the bladder to fit the contour of a user.

25. A device according to claim 7 wherein the visual indicator comprises a bar graph indicative of the applied force.

26. A method according to claim 21, wherein the feedback comprises an indication of a strength level measured on a non-linear scale.

27. A method according to claim 26, wherein the non-linear scale comprises a user-selected non-linear scale and the method comprises receiving a selection of the user-selected non-linear scale from among a plurality of nonlinear scales.

28. A method according to claim 26, wherein the non-linear scale comprises an automatically selected non-linear scale and the method comprises automatically selecting the non-linear scale from among a plurality of nonlinear scales based on characteristics of the user.

29. A method according to claim 26 wherein providing feedback comprises providing audible feedback.

30. A method according to claim 26 wherein providing feedback comprises providing visual feedback.

31. A method according to claim 26 wherein the raised section comprises an inflatable bladder, the method comprising automatically inflating or deflating the inflatable bladder to a desired pressure.

* * * * *